United States Patent [19]

Chester

[11] Patent Number: 4,694,826

[45] Date of Patent: Sep. 22, 1987

[54] ENDOTRACHEAL TUBE GUIDE

[75] Inventor: Martin H. Chester, Carmel, Calif.

[73] Assignee: Carmel Medical Devices, Carmel, Calif.

[21] Appl. No.: 670,850

[22] Filed: Nov. 13, 1984

[51] Int. Cl.$^4$ ............................................. A61B 17/00
[52] U.S. Cl. .................................. 128/303 R; 128/20
[58] Field of Search ............ 128/3, 20, 303 R, 200.26, 128/207.14–207.15, DIG. 26, 17

[56] References Cited

U.S. PATENT DOCUMENTS

| | | | |
|---|---|---|---|
| 730,284 | 6/1903 | Monosmith | 128/17 |
| 762,743 | 6/1904 | McDade | 128/17 |
| 2,756,742 | 7/1956 | Barton | 128/207.14 X |
| 3,651,800 | 3/1972 | Wilbanks | 128/20 X |
| 3,701,348 | 10/1972 | Navara | 128/20 |
| 3,754,554 | 8/1973 | Felbarg | 128/200.26 |
| 3,946,742 | 3/1976 | Eross | 128/DIG. 26 X |
| 4,211,234 | 7/1980 | Fisher | 128/200.26 |
| 4,329,983 | 5/1982 | Fletcher | 128/207.15 X |
| 4,481,947 | 11/1984 | Chester | 128/20 X |

FOREIGN PATENT DOCUMENTS

| | | | |
|---|---|---|---|
| 1535060 | 12/1978 | United Kingdom | 128/200.26 |
| 0182293 | 7/1966 | U.S.S.R. | 128/303 R |

OTHER PUBLICATIONS

V. Mueller and Co. Catalogue, 1929, p. 232.
Stainless Steel Retractors; Scanlon-Morris Co. brochure (Stille Division), pp. 2-4.
Murray-Baumgartner Surgical Instrument Co. catalogue 1934.
Charles Traux Greene and Co. catalogue.
Mueller & Co.; "Eye Instruments", 1938 catalog.
Mueller; "The Surgical Armamentarium", 1981, pp. 861, 769, 752, 698, 369, 347, and 186.
Padberg et al.; "Molded Lucite Surgical Instruments"; J. of the Amer. Med. Assoc.; 7/12/52, pp. 1018-1019.
Codman Gen'l. Surg. Instruments catalog, 1973, pp. 83, 193.
Chester; "A New Endotracheal Tube Retractor"; Anesthesiology vol. 51, 1979, p. 274.

Primary Examiner—Lee S. Cohen
Assistant Examiner—Angela D. Sykes
Attorney, Agent, or Firm—Sughrue, Mion, Zinn, Macpeak & Seas

[57] ABSTRACT

An endotracheal tube guide has a lower blade portion of generally semicircular configuration which permits an endotracheal tube guide to be manipulated or guided in the posterior direction during intubation, as well as in the anterior, lateral and medial directions. The tube has an angled handle extending in a direction opposite from that of the blade portion such that the user's hand will not obstruct the view of the endotracheal tube guide being engaged by the guide.

7 Claims, 8 Drawing Figures

U.S. Patent  Sep. 22, 1987  4,694,826
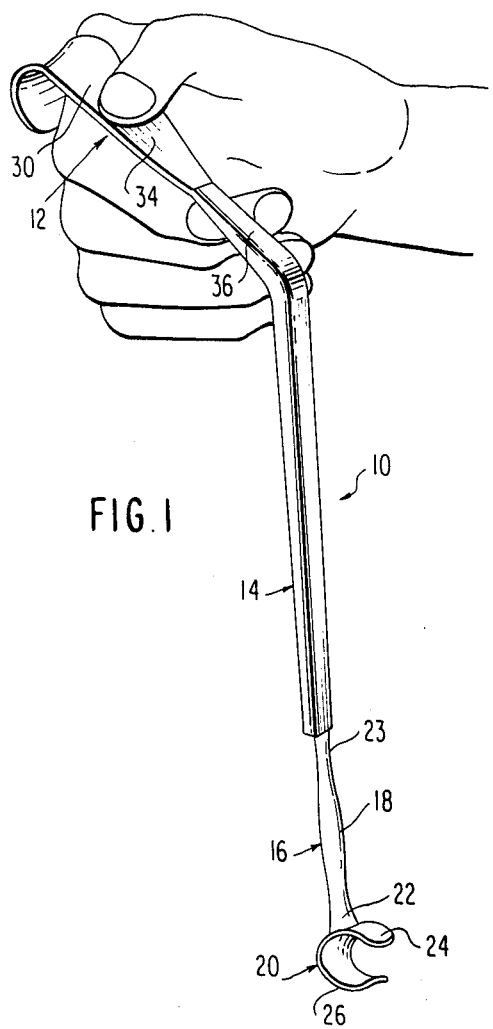
FIG. 1
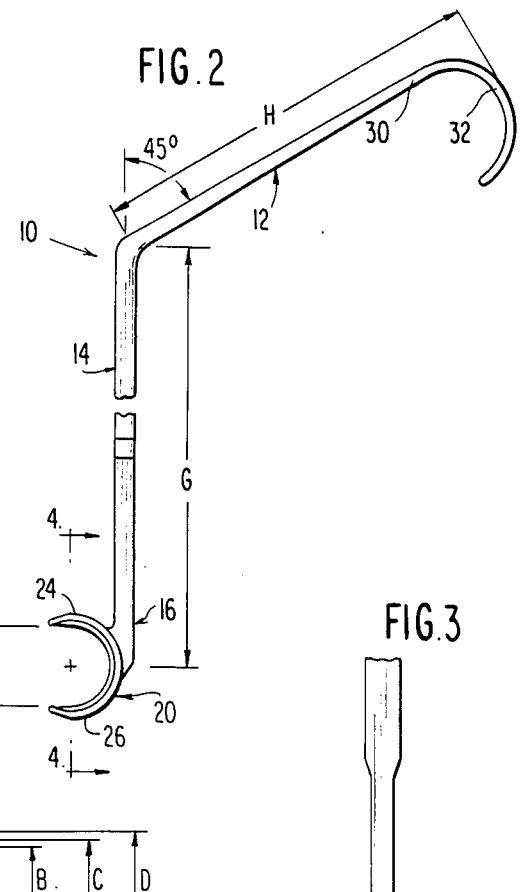
FIG. 2
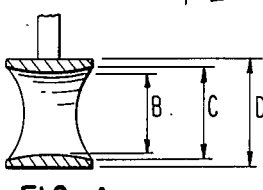
FIG. 4
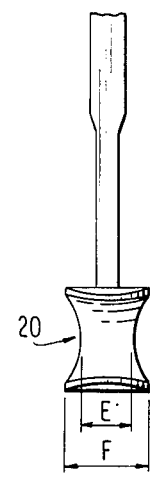
FIG. 3
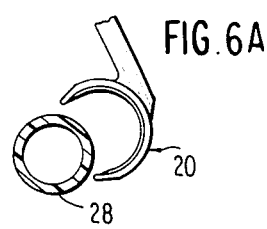
FIG. 5
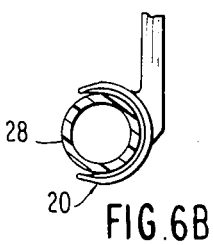
FIG. 6A
FIG. 6B
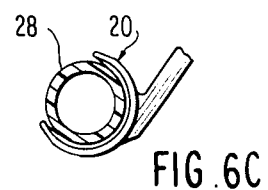
FIG. 6C

ENDOTRACHEAL TUBE GUIDE

CROSS-REFERENCE TO RELATED APPLICATION

Ser. No. 121,620, filed Feb. 14, 1980, now U.S. Pat. No. 4,481,947.

BACKGROUND OF THE INVENTION

1. Field of the Invention

The invention relates generally to the field of endotracheal intubation, and more particularly, to an endotracheal tube guide especially useful in facilitating nasotracheal intubation of patients under either direct vision laryngoscopy or blind techniques.

2. Description of the Prior Art

The intubation of patients is a technique well known in the anesthesia and medical arts and involves the insertion of an endotracheal tube into the trachea through either the nose or mouth. In the direct technique, the tip of the endotracheal tube is observed with a laryngoscope as the tube progresses down the posterior pharynx into the glottis, through the vocal cords and into the trachea. During nasotracheal intubation, it is often necessary to guide the endotracheal tube into the glottis with the aid of forceps. In intubation of this type, the visible end of the endotracheal tube is grasped with the forceps, and the practitioner controls the direction of the tip of the tube in order to guide it into the glottis and through the vocal cords.

In the blind technique, the tube direction is changed by flexion, extension, or rotation of the head, as the blind application of forceps is extremely hazardous and is of no value in facilitating blind intubation.

U.S. Pat. No. 3,701,348 to Navara discloses a tool used for pathological procedures, such as the opening of the skull. To this end, the device of Navara is provided with a relatively flat elongated center portion, a flat chiseled portion formed on one end of the center portion, and a curved retractor portion formed on the other end of the central portion. As seen in FIG. 1 of the patent, the retractor portion 17 comprises an inwardly curved member and is of about the same length as the chisel portion 15. In use, a cut is made in the skull by a suitable high velocity saw. The chiseled portion 15 is inserted into the groove made by the saw blade, and is then laterally moved to separate the parts of the skull by prying. The retractor portion 17 is then used to hook an edge of the severed portion, and to remove the same. However, while the device disclosed by Navara may have certain utility as a skull retractor, it is much larger than anything which would be usable for tracheal work.

The V. Mueller & Co. Catalogue (1929) at page 232 discloses two types of retractors for use in tracheal work. The retractor A8535, known as Shurly's retractor, consists merely of a flat length of sheet steel with a bend in one end. This type of retractor has distinct disadvantages in that the central gripping portion thereof is wide and flat and is, therefore, difficult to delicately manipulate by the practitioner. Further, as the handle portion of this retractor is straight, rather than angled, the hand which normally grips and guides the retractor will necessarily often obstruct the view of the user. Model No. A8540 of the same catalogue shows a retractor which has a long slim tapered handle which allows for easy manipulation by the user. However, as the handle portion is straight, the user's hand will still often block a direct view of the endotracheal tube. Further, the tube engaging portion of this retractor is formed generally in the shape of a common fork, with the tines curled around in order to make a scoop-like shape. Thus, this retractor is extremely unsuitable for use in the blind technique, as the sharp tips of the tines are likely to engage and tear the tissue surrounding the area adjacent the endotracheal tube.

The Scanlon-Morris Co. Brochure (Stille Division) discloses at pages 2, 3 and 4 thereof a plurality of retractors for geneal use. The Model No. 86-54 retractor is disclosed as being for tracheal use. However, the design of this tracheal retractor is very similar to the previously mentioned Mueller retractor in that the endotracheal tube-engaging portion is provided with sharp tips and is, therefore, of no utility in a blind intubation technique. The Model No. 46-88retractor is a large liver retractor having a hollow handle.

The Murray-Baumgartner Surgical Instrument Co. Catalogue (1934) again discloses a plurality of retractors for general surgical use. Of particular interest are the Model Nos. 2149-2152 which display a curved scoop-shaped retractor blade portion. However, it is noted that the handles of these retractors are thin, flat, and of an overall arcuate shape and, therefore, have the same disabilities for delicate work as do the previously mentioned Mueller retractors.

The Charles Truax Greene & Co. Catalogue depicts a plurality of retractors for use in gynecology. FIG. 7233 of this Catalogue depicts a retractor which has a generally scoop-shaped end. However, the handle of this retractor does not allow the practitioner to grip and manipulate the device in a manner such that the practitioner's hand would not obstruct his view of an endotracheal tube.

The Journal of the American Medical Association, July 12, 1952, contains an article on pages 1018 and 1019 thereof which discusses the use of various types of generally S-shaped retractors formed of lucite. However, it is noted that none of the retractors disclosed in this article has a blade having upper and lower blade portions whose junction is attached to a thin elongated generally cylindrical gripping portion.

The Codman General Surgical Instruments Catalog, cover page, and pages 83 and 193 (1973) relate to an atrial retractor, not to an endotracheal tube guide. Atrial retractors are used to retract the atrium during cardiac surgery. The extremely large handle of the atrial retractor of FIG. B is used so as largely to eliminate arm and finger fatigue in the surgeon using the retractor for extended period of time. A constant pull with a minimum amount of movement is required in the use of such retractors, and the manipulability of the retractor is not of primary importance. In the retractor of FIG. A of page 193, the handle portion is knurled so as to allow the surgeon firmly to grip the instrument, but, again, the manipulability of the instrument is not of primary importance.

USSR Patent No. 182293 shows a surgical instrument having a double bend in the handle thereof for facilitating visual observation during intra-aural operations.

The publication, Anesthesiology, volume 51: 274, 1979 contains on page 274 thereof a disclosure of applicant's endotracheal tube retractor which is the subject of the above cross-referenced copending patent application. This retractor cannot easily guide an endotracheal tube in the posterior direction. Furthermore, the retractor handle must be rotated to guide the endotracheal tube in a right or left lateral direction. This maneuver may occlude the field of vision in some instances.

SUMMARY OF THE INVENTION

The primary object of the invention is to provide an improved endotracheal tube guide whose distal end is shaped so that it engages a endotracheal tube such that the tip of the tube may be moved in the lateral, anterior and posterior directions.

A more specific object is to form the distal end of the guide in the form of a generally semi-circular blade having upper and lower blade portions which, together, subtend an angle of slightly more than 180°.

Still another object of the invention is to provide such a guide in which the distal end of the handle joins the blade at the junction of the two blade portions.

A further object of the invention is to provide the guide with an angled handle which permits the use of the guide for either direct or blind intubation and also provides a means by which the physician can firmly grip the guide while at the same time easily manipulating it.

BRIEF DESCRIPTION OF THE DRAWING

FIG. 1 is a perspective view of an endotracheal tube guide embodying the present invention;

FIG. 2 is a partial sideview showing the configuration of the blade at the distal end of the guide and also the point at which the guide handle joins the blade;

FIG. 3 is a front view of the blade of the guide;

FIG. 4 is a cross-sectional view taken along line 4—4 of FIG. 2;

FIG. 5 is a diagrammatical illustration showing the manner in which the guide is used in endotracheal intubation;

FIGS. 6A, 6B and 6C are partial side views showing various angular positions of the guide for engaging and moving an endotracheal tube.

DETAILED DESCRIPTION OF THE INVENTION

In the drawing, the numeral 10 generally designates an endotracheal tube guide embodying my invention. The guide 10 has an angled handle portion 12, a rectangular midsection 14, and a lower blade section 16.

The blade section 16 has a generally cylindrical shaft 18 joined to the lower end of the midsection 14. Joined to the lower end of the shaft 18 is a generally semi-circular blade 20 for engaging an endotracheal tube. The shaft 18 has a lateral dimension which is generally smaller than that of the midsection 14; however, the lower portion 22 of shaft 18 is flat and tapers outwardly to have a width substantially the same as that of the blade 20 at the junction of the blade and shaft 18. The generally cylindrical center portion of shaft 18 has a larger diameter than that of its upper portion 23 and of the portion between the center portion and the flat portion 22.

The blade 20 is of generally semi-circular configuration and has an upper lip 24 and a lower lip 26. The lips converge toward each other to form an opening having a dimension A which is just slightly larger than the external diameter of the endotracheal tube 28 which is to be guided.

All edges of the blade are smooth and rounded to form blunt edges so that the instrument has no sharp edges or points which could otherwise injure the tissue surrounding the area of operation. Such a feature is of magnified importance when the "blind" intubation technique is employed.

The angled handle 12 forms an angle of approximately 45° with the midsection 14 and terminates in a flattened hook portion 30 having a saddle-shaped or concave shape for accommodating the thumb of the physician as illustrated in FIG. 1. The end of the hook portion 30 has a hook 32 for engaging the back of the index finger of the physician, as illustrated in FIG. 1. The width and concavity of the hook portion 32 is chosen such as to accommodate the thumb and index finger of a physician. The portions of the handle section 12 which are engaged by the physician's hand are finely knurled to improve grippability.

As shown in FIG. 1, the handle portion 12 is designed to be gripped by the user such that, with the hand in a slightly closed position, the thumb rests on the concave top surface 34, while the back of the index finger is engaged by the hook 32. The index finger extends along the lower surface of hook portion 30 to provide a firm grip when the thumb and index finger are pressed together. Since the guide 10 is symmetrical, it may be used with equal dexterity in either hand of the physician.

The primary advantage of such an angled handle is that it allows the physician firmly to grip the instrument, while at the same time avoiding the possibility of the hand or fingers obstructing the view of the endotracheal tube, the epiglottis or the larynx, etc. Therefore, the physician is provided with an excellent, unobstructed view, even while the endotracheal tube is being guided or manipulated into the desired position.

In operation, as illustrated in FIG. 5, the endotracheal tube 28 is passed through the nose or mouth until the tip 40 of the tube is visualized or palpated with the examining finger in the posterior pharynx in the area of the endotracheal tube above the cuff 38 thereof. Then, the physician rotates the handle to an angular position as shown in FIG. 6A and moves the blade 20 towards the tube until the tube is engaged within the blade. The handle is then rotated to the position shown in FIG. 5 and FIG. 6B, in which position downward movement along the axis of the handle midsection 14 causes the upper blade lip 24 to engage the top of the tube 28 so that the tip 40 of the tube may be guided or manipulated in the posterior direction. Upward movement of the handle midsection causes the lower lip 26 of the blade 20 to engage the lower surface of the tube, thereby permitting the tip 40 of the tube to be adjusted in the anterior direction; in this position of the guide, the tube can also be moved in the lateral or medial direction (i.e. out of the plane of the paper in FIG. 5), by causing the back of the blade 20 to bear against the surface of the tube. When the handle is rotated to the position shown in FIG. 6C, the tube can be moved in the opposite lateral or medial direction (i.e. to the right in FIG. 6C or into the plane of the paper in FIG. 5), because the tip of the lower blade portion 26 is rotated several degrees counterclockwise from the position shown in FIG. 6B and, thereby, bears against the surface of the tube to permit such lateral or medial movement.

When the direct vision technique is utilized, the tube may be engaged by the instrument under direct vision with the use of a laryngoscope. If the blind technique is used, the retractor blade may be guided by the examining finger. As mentioned previously, the conventional technique of blind intubation, well known in the anesthesiology art, requires the flexing, extending, or rotation of the head. However, by using the instrument of the present invention, this requirement of movement is obviated, as the direction of the tip of the endotracheal tube may be changed by moving the retractor in a lateral, medial, posterior, or anterior direction. Therefore, the tip 40 of the endotracheal tube may be easily moved in the posterior direction, a function which is very advantageous if the tip of the tube gets caught in the pharyngo-epiglottic fold and has to be moved posteriorly to direct it into the inlet of the larynx. More specifically, it is a common difficulty to have the tube tip 40 impinge in the sulcus, between the base of the tongue and the epiglottis, and be stopped. However, using the tube guide 10 of this invention, the physician causes the guide blade 20 to engage the tube 28 and then directs or guides the tip 40 in a posterior direction into the entrance of the larynx. This technique of blind endotracheal intubation is especially useful with patients with anatomical deformities, such as a spur on the second or third cervical vertebra protruding into the nasopharynx or oropharynx, tumor formation in the posterior pharynx, and fracture-luxation of the cervical spine column. In conditions, such as ankylosing spondylitis of the cervical spine and cervical traction, where the head is immobilized, endotracheal intubation is facilitated by the use of the retractor.

After the endotracheal tube is successfully passed through the vocal cords and into the trachea of the patient, the retractor may be disengaged from the tube by shifting the retractor handle towards the midline so as to release the tube from the blade.

As shown in FIGS. 2, 3 and 4, the generally semicircular blade 20 subtends an arc of slightly more than 180° with the free ends of the upper and lower lips 24 and 26 converging toward each other. Furthermore, and as best shown in the cross-sectional view of FIG. 4, the thickness of the inner portions of the lips 24 and 26 increases towards the center in order to form convex surfaces so that the lips will engage the tube 28 with substantially a line contact. Also, the free ends of the tips are wider than the ends fixed to the lower shaft portion 22, the tapering of the width being shown in FIGS. 3 and 4.

The guide 10 may be made in four different sizes: Adult, small adult, pediatric and infant, with dimensions generally diminishing in the direction from the adult to the infant size. Some typical dimensions are shown in the following table where all dimensions are in inches.

|  | A | B | C | D | E | F | G | H |
|---|---|---|---|---|---|---|---|---|
| ADULT | .600 | .610 | .650 | .740 | .400 | .625 | 7.500 | 3.000 |
| SMALL ADULT | .428 | .492 | .534 | .624 | .300 | .469 | 6.000 | 3.000 |
| PEDIATRIC | .357 | .376 | .406 | .496 | .250 | .375 | 4.000 | 3.000 |
| INFANT | .250 | .256 | .286 | .376 | .187 | .312 | 3.000 | 3.000 |

The foregoing is to be considered as illustrative only of the principles of the invention. Further, since numerous modifications and changes will readily occur to those skilled in the art, it is not desired to limit the invention to the exact construction shown and described, and, accordingly, all suitable modifications and equivalents may be resorted to and still fall within the scope of the invention which is limited only as defined in the following claims.

I claim:

1. An endotracheal tube guide for easily guiding an endotracheal tube in the posterior, anterior, lateral and medial directions during intubation, said guide comprising:

lower blade portion means having a generally semicircular configuration for engagement with an endotracheal tube during intubation and having an upper and a lower curved lip portion which defines said semicircular configuration;

an elongated middle portion connected to said blade portion means at an upper end of said blade portion means; and handle portion means connected at a lower end thereof to an upper end of said middle portion and being oriented at an acute angle with respect to the longitudinal axis of said middle portion, said handle portion means and said semicircular blade portion means extending away from said longitudinal axis of said middle portion in opposite directions;

said handle portion means being of sufficient length to form a gripping portion engageable between the thumb and index finger of one hand such that, when gripped, neither the hand nor the fingers of the hand extend substantially beyond a plane defined by a front face of said middle portion, and such that the index finger extends along a lower surface of said handle portion means and the thumb presses against a top surface of said handle portion means.

2. The endotracheal tube guide as defined in claim 1 wherein said semicircular blade portion means subtends an arc of more than 180°, and wherein said lip portions have free ends which converge towards each other to form blade opening means having a longitudinal dimension only slightly larger than the diameter of the endotracheal tube to be engaged.

3. The endotracheal tube guide as defined in claim 2 wherein each of said lip portions has an inwardly radially directed convex surface for forming a line contact with an engaged endotracheal tube.

4. The endotracheal tube guide as defined in claim 1 wherein said acute angle is approximately 45°.

5. The endotracheal tube guide as defined in claim 4 wherein a free end of said handle portion means has a hook portion which is adapted to engage the back of the index finger.

6. The endotracheal tube guide as defined in claim 5 wherein said semicircular blade portion means subtends an arc of more than 180°, and wherein said lip portions have free ends which converge towards each other to form blade opening means having a longitudinal dimension only slightly larger than the diameter of the endotracheal tube to be engaged.

7. The endotracheal tube guide as defined in claim 4 wherein said top surface of said handle portion means is knurled and has a downwardly directed concavity for receiving the thumb.

* * * * *